United States Patent
Goldfarb et al.

(10) Patent No.: US 8,623,098 B2
(45) Date of Patent: Jan. 7, 2014

(54) SYSTEMS AND METHOD FOR VOLITIONAL CONTROL OF JOINTED MECHANICAL DEVICES BASED ON SURFACE ELECTROMYOGRAPHY

(75) Inventors: Michael Goldfarb, Franklin, TN (US); Huseyin Atakan Varol, Nashville, TN (US); Kevin Ha, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/150,773

(22) Filed: Jun. 1, 2011

(65) Prior Publication Data
US 2012/0004736 A1    Jan. 5, 2012

Related U.S. Application Data

(60) Provisional application No. 61/360,676, filed on Jul. 1, 2010.

(51) Int. Cl.
*A61F 2/70* (2006.01)
(52) U.S. Cl.
USPC ............................................... 623/25
(58) Field of Classification Search
USPC ................... 623/24, 25, 40, 47, 50
See application file for complete search history.

(56) References Cited

U.S. PATENT DOCUMENTS

| | | |
|---|---|---|
| 5,246,465 A | 9/1993 | Rincoe et al. |
| 2008/0071386 A1* | 3/2008 | McBean et al. ............. 623/25 |
| 2009/0143870 A1 | 6/2009 | Bedard et al. |
| 2009/0265018 A1 | 10/2009 | Goldfarb et al. |

FOREIGN PATENT DOCUMENTS

WO     2011/066940 A1    6/2011

OTHER PUBLICATIONS

Dudley S. Childress, Ph. D., Engineering in Medicine and Biology Magazine, "Myoelectric Control of Powered Prosthesis", Dec. 1982.
Max Donath, B. Eng., McGill University, "Proportional EMG Control for Above Knee Prosthesis", Aug. 1974.
PCT international Search Report and Written Opinion mailed Oct. 19, 2011. In corresponding application No. PCT/US2011/038705.

* cited by examiner

*Primary Examiner* — Bruce E Snow
(74) *Attorney, Agent, or Firm* — Novak Druce Connolly Bove + Quigg LLP

(57) ABSTRACT

Systems and methods for controlling a weight bearing member having at least one powered joint are provided. A system includes a velocity reference module for receiving myoelectric control signals from a user during a non-weight bearing mode for the powered joint and generating a velocity reference for the powered joint based on the myoelectric control signals. The system further includes a volitional impedance module for generating a torque control signal for actuating the powered joint based at least on the velocity reference.

9 Claims, 11 Drawing Sheets

SYSTEMS AND METHOD FOR VOLITIONAL CONTROL OF JOINTED MECHANICAL DEVICES BASED ON SURFACE ELECTROMYOGRAPHY

CROSS-REFERENCE TO RELATED APPLICATION

This application claims the benefit of Provisional Application Ser. No. 61/360,676 entitled "VOLITIONAL CONTROL OF PROSTHETIC AND ORTHOTIC LOWER LIMB DEVICES USING MYOELECTRIC SIGNALS", filed Jul. 1, 2010, which is herein incorporated by reference in its entirety.

STATEMENT REGARDING FEDERALLY SPONSORED RESEARCH

This invention was made with U.S. government support under grant number NIH RO1EB005684. MG which was awarded by the National Institutes of Health. The U.S. government has certain rights in the invention.

FIELD OF THE INVENTION

The present invention relates to control of jointed mechanical devices, and more specifically to systems and methods for controlling jointed mechanical devices based on surface electromyography.

BACKGROUND

Although prosthetic knee joints for transfemoral prostheses have traditionally been energetically passive devices, powered, semi-autonomous knee joints have recently started to emerge in the research community and on the commercial market. Typically, passive knee prostheses can only react to mechanical energy imparted by the amputee, while powered knee prostheses have the ability to act independently of mechanical energy from the user. As such, the nature of the user communication with the powered prosthesis and control of the powered prosthesis is substantially different from the control of a traditional, energetically passive prosthesis.

Various methods have been proposed for the control of powered knee prostheses. These approaches typically utilize instrumentation on at least one of the prosthesis or a sound leg. Such instrumentation can include inertial measurement sensors (accelerometers and/or gyroscopes) at the foot, shank or thigh of the prosthesis and/or sound side. Additionally, joint angular position, velocity and torque sensors for ankle, knee and hip joints of the prosthesis and/or sound side can also be used as instrumentation for prosthesis control. Further, ground force detecting load cells or load switches can also be used to detect events such as heel strike or toe-off. This instrumentation is used to form knee joint angle trajectories or impedances for the powered knee prosthesis during activities involving the prosthesis. For example, while standing, walking, or transitioning between sitting and standing.

In general, activities such as standing, walking, or transitioning between sitting and standing all involve physical input and/or energy exchange between the residual limb and prosthesis. Therefore, most conventional methods rely on some form of physical input from the user for communication with the powered knee prosthesis. That is, although the user need not provide the energy for movement, as is the case with traditional dissipative knee prostheses, the user must still provide some physical input that can be measured by instrumentation on the prosthesis and/or sound leg. Such physical inputs include measuring weight bearing on the prosthesis, torque and/or acceleration from the affected-side hip joint, movement of the sound-side leg, to name a few.

An important class of movement, however, which does not involve any significant physical input from the user, is the task of non-weight-bearing or volitional control of knee movement while sitting or standing. That is, people regularly shift their body while sitting, which involves significant movement of the knee joints. Such movement has both physiological and practical purposes. Regarding the former, weight shifting during sitting is known to play an important role in ensuring healthy circulation of blood in weight-bearing tissues during sitting. Regarding the latter, sitting in confined areas, such as in automobiles, airplanes, theatres, and classrooms, often requires shifting of body position (particularly of the knee joints) in order to accommodate a particular ergonomic space and/or the movement of other individuals into or out of that space. Such movement is referred to herein as volitional control of the knee joint during non-weight-bearing activity. Note that such volitional control is also useful in non-weight-bearing standing, such as when flexing the knee to look at the bottom of a shoe, or when placing the foot on an elevated surface (such as a chair) to tie or untie, or don or doff a shoe. In the case of a traditional, energetically passive prosthesis, an amputee typically achieves "volitional" control functionality by manipulating the prosthetic knee leg with his or her hands.

SUMMARY

The various embodiments present systems and methods for the volitional control of the knee joint during non-weight-bearing activity which utilizes a pair of surface electromyogram (EMG) electrodes (on the ventral and dorsal aspects of the thigh, respectively), such as that integrated into the amputee's socket interface. Such an approach can be integrated with the impedance-based weight-bearing controllers for standing, walking, and transitioning between sitting and standing in order to provide volitional control of the knee joint during non-weight-bearing activity.

Researchers have investigated the use of surface EMG for the control of lower limb prostheses and orthoses. In the case of passive knee prostheses, Some groups have developed a prosthesis with an electrically activated knee flexion lock, and used surface EMG from the residual limb of a transfemoral amputee to trigger the engagement and disengagement of the lock. Other groups developed a computer-controllable passive knee prosthesis based on an electrically modulated brake, and utilized surface EMG from three sites on the residual limb of a transfemoral amputee for gait mode recognition, which in turn was used to switch the prosthesis into the appropriate gait mode. Yet other groups utilized surface EMG from multiple electrodes on transfemoral amputees to classify movement intents while walking. With regard to using EMG for the real-time control of a powered knee prosthesis, one group has attempted to use surface EMG from the quadriceps and hamstrings to control the motion of a hydraulically actuated powered knee prosthesis during walking. However, this group concluded that use of such an approach during gait would be challenging, due in part to difficulty in obtaining reliable EMG measurement, "due to noise pick up and movement artifact." Other groups have used surface EMG measured from the lower leg for the control of powered ankle joints in transtibial prostheses, or powered joints in ankle-foot-orthoses (AFOs). For example, one group has proposed the use of EMG measured from the lower leg to control the assistive pressure in a pneumatically actuated AFO. Another group has proposed a control system for an assistive exoskeleton with powered hip and knee joints, in which the assistive torque from the exoskeleton is proportional to the measured EMG from the associated flexion or extension muscle group. However, the methods and techniques described above do not disclose utilizing EMG for the volitional control of knee or ankle joint motion in a powered prostheses.

In contrast, the various embodiments of the invention concern systems and methods for controlling jointed mechanical devices, such as prostheses and orthoses, based on surface electromyography. In particular, providing volitional control of powered joints. In a first embodiment, a myoelectric controller for a weight bearing member having at least one powered joint is provided. The myoelectric controller includes a velocity reference module for receiving myoelectric control signals from a user during a non-weight bearing mode for the powered joint and generating a velocity reference for the powered joint based on the myoelectric control signals. The controller further includes a volitional impedance module for generating a torque control signal for actuating the powered joint based at least on the velocity reference.

In a second embodiment of the invention, a method for controlling at least one powered joint in a weight bearing member is provided. The method includes the step of receiving myoelectric control signals from user during a non-weight bearing mode for the powered joint. The method also includes generating a velocity reference for the powered joint based on the myoelectric control signals. The method further includes generating a torque control signal for actuating the powered joint based at least on the velocity reference.

In a third embodiment of the invention, a jointed mechanical device is provided. The device includes a weight bearing member comprising at least one powered joint. The device also includes a controller for actuating the powered joint. In the device, the controller is configured for actuating the joint in at least one of a semi-autonomous weight bearing mode and a non-weight bearing mode for actuating the powered joint responsive to myoelectric control signals.

In a fourth embodiment of the invention, a computer-readable medium is provided, storing instructions for controlling a computing device to control a powered joint. The instructions include instructions for receiving myoelectric control signals from user during a non-weight bearing mode for the powered joint, generating a velocity reference for the powered joint based on the myoelectric control signals, and generating a torque control signal for actuating the powered joint based at least on the velocity reference.

Thus, a control approach is provided that not only provides the above-mentioned benefits of volitional control for amputees, but also provides such volitional control in a manner that the trajectory tracking performance is close to that observed in intact or sound joints.

DETAILED DESCRIPTION

Figure 1:
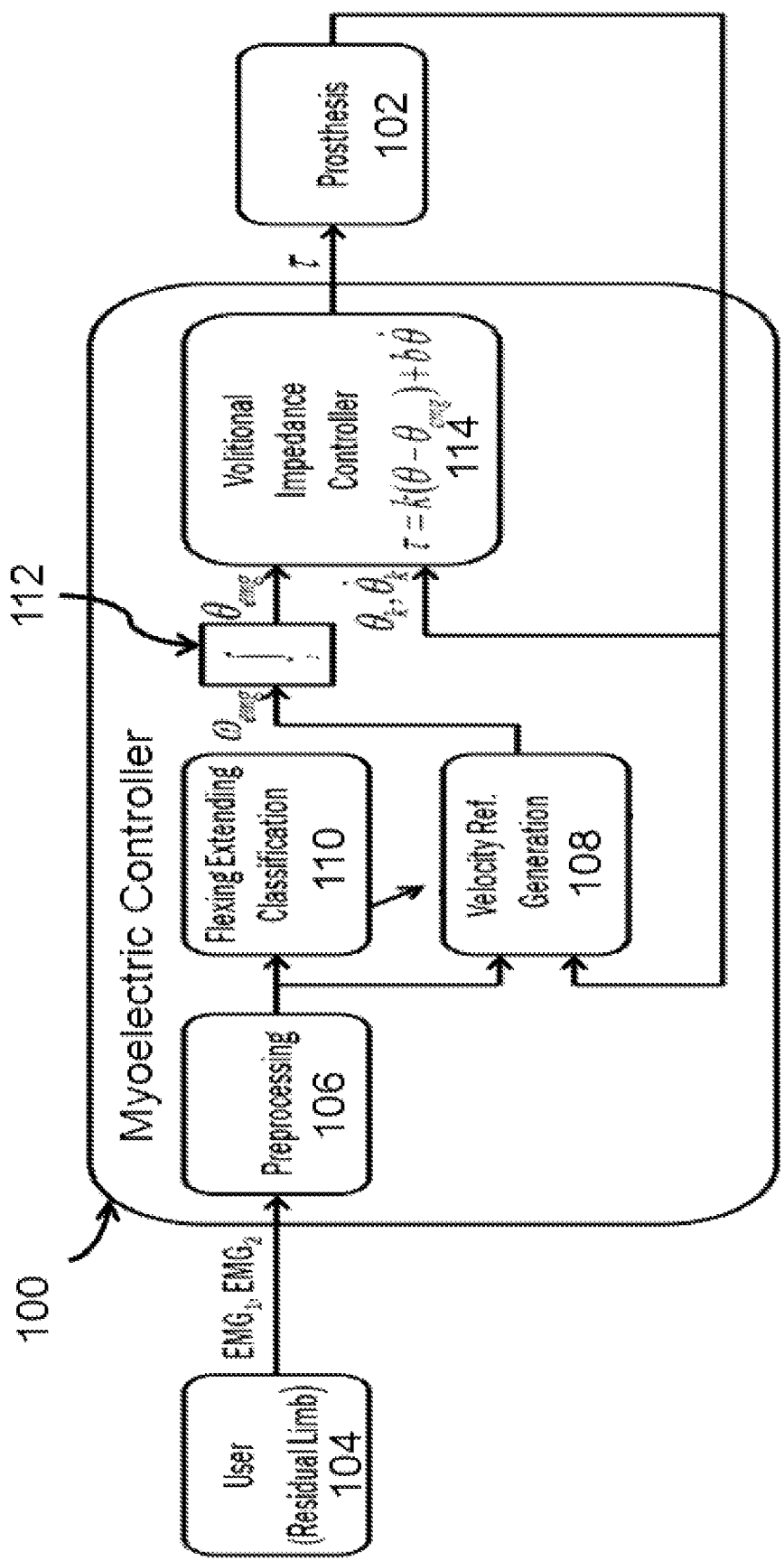
FIG. 1 shows a block diagram of a myoelectric volitional impedance controller for controlling a powered knee joint in accordance with an embodiment.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As described above, in a traditional, energetically passive prosthesis, an amputee can achieve volitional control functionality by manipulating the prosthetic knee leg with his or her hands. However, since a powered knee prosthesis has the capability to move itself, such artificial manipulation should not be required for volitional movement of the knee joint. Nonetheless, since such volitional movements do not involve significant physical input from the amputee, conventional control approaches do not provide an effective means of communication with the prosthesis for this purpose.

In view of the limitations of conventional control approaches and conventional prostheses, the various embodiments provide a new method for the volitional control of the knee joint during non-weight-bearing activities. More generally, the various embodiments provide systems and methods controlling jointed mechanical devices, such as prostheses and orthoses, during non-weight bearing activities based on a volitional impedance control framework.

For example, in the case of a leg prosthesis, this allows a transfemoral amputee to control the motion of a powered knee prosthesis during non-weight-bearing activity (e.g., while sitting.). The control is based on an impedance framework wherein the joint exhibits programmable joint stiffness and damping characteristics. Knee movement is provided by commanding the joint stiffness equilibrium angle. The time rate of change of this angle (which is the desired angular velocity set-point) is provided by measurement of the surface EMG, using a pair of surface electromyogram (EMG) electrodes. In one embodiment, the electrodes can be on the ventral and dorsal aspects of the thigh. For example these electrodes can be integrated into the amputee's socket interface so as to measure the surface EMG of the hamstring and quadriceps muscle groups. However, rather than directly associate the hamstring EMG with knee flexion and the quadriceps with knee extension, which would require the user to artificially isolate contraction of these muscle groups, the various embodiments incorporate a combination of pattern classification and principal component projection to align the measured EMG with the user's desire to flex or extend the knee joint. The resulting control approach provides trajectory tracking performance close to that of intact knee joints, thus providing an approach for effective control of knee joint motion during non-weight-bearing activity. Further, this approach can be integrated with existing impedance-based weight-bearing controllers for standing, walking, and transitioning between sitting and standing. For example, this approach can be integrated into the controller described in U.S. patent application Ser. No. 12/427,384 to Goldfarb et al, filed Apr. 21, 2009, the contents of which are herein incorporated in their entirety.

Although exemplary embodiments will be described primarily with respect to providing volitional control for a prosthesis including at least a powered knee, the various embodiments are not limited in this regard. Rather, the framework described herein can be used for volitional control of any type of powered joint in a prosthesis or an orthosis.

The use of surface EMG for the control of lower limb prostheses and orthoses has been widely investigated. In the case of passive knee prostheses, one existing approach provides a prosthesis with an electrically activated knee flexion lock that uses surface EMG from the residual limb of a transfemoral amputee to trigger the engagement and disengagement of the lock. A similar approach includes a computer-controllable passive knee prosthesis based on an electrically modulated brake, and utilizes surface EMG from three sites on the residual limb of a transfemoral amputee for gait mode recognition, which in turn was used to switch the prosthesis into the appropriate gait mode. More recently, surface EMG from multiple electrodes on transfemoral amputees has been utilized to classify movement intents while walking. However, with regard to using EMG for the real-time control of a powered knee prosthesis, only limited investigation into the use of surface EMG from the quadriceps and hamstrings to control the motion of a hydraulically actuated powered knee prosthesis during walking has occurred. Further, such research concluded that use of such an approach during gait would be challenging, due in part to difficulty in obtaining reliable EMG measurement, "due to noise pick up and movement artifact."

Other conventional control methodologies using surface EMG measured from the lower leg have been generally directed to the control of powered ankle joints in transtibial prostheses or control of powered joints in ankle-foot-orthoses (AFOs). With regard to the former, one approach provides for using a real-time state-based controller for the powered ankle based on physical input (rather EMG input) from the user and which utilizes EMG measured from the lower leg to switch between gait modes. With regard to powered AFOs, one approach uses EMG measured from the lower leg to control the assistive pressure in a pneumatically actuated AFO. Additionally, a control system for an assistive exoskeleton with powered hip and knee joints has been proposed, in which the assistive torque from the exoskeleton is proportional to the measured EMG from the associated flexion or extension muscle group. However, none of these approaches utilize EMG for the volitional control of knee joint motion in a powered knee prosthesis.

Volitional Control of Powered Knee

A. Volitional Control Structure

In a first exemplary embodiment, a control framework is provided for volitional control of the knee with a joint output impedance similar to that of the native limb. As such, rather than using the measured EMG to prescribe joint torque, angle, or angular velocity, the presented framework utilizes measured EMG to prescribe the angular velocity of an equilibrium point of joint impedance that consists of the combination of a joint stiffness and damping. In this manner, the knee moves to a desired position with a joint output stiffness and damping prescribed by the controller, thus presumably moving in a more natural manner (relative to a high-output-impedance position controller), and resulting in a more natural interaction between the user, prosthesis, and environment.

The structure of the proposed volitional controller is shown in FIG. 1. FIG. 1 shows a block diagram of a myoelectric volitional controller 100 for controlling a powered knee joint in a prosthesis 102 based on EMG signals from a user 104 in accordance with an embodiment. In this controller, a real-time intent recognizer, such as the one described in U.S. patent application Ser. No. 12/427,384 to Goldfarb et al, filed Apr. 21, 2009, or in Varol, H. A., Sup, F., and Goldfarb, M. Multiclass Real-Time Intent Recognition of a Powered Lower Limb Prosthesis. IEEE Transactions on Biomedical Engineering, vol. 57, no. 3, pp. 742-751, 2009 would be used to switch between this (volitional) controller and other weight-bearing control structures.

With reference to FIG. 1, the controller 100 operates as follows. First, during a non-weight bearing activity, based on an intent recognizer (not shown), EMG signals ($EMG_1$, $EMG_2$) are received by controller 100 from the residual limb of the user 104. Thereafter, a pre-processing module 106 processes the EMG signals. The pre-processed signals are then used for generation of reference velocity (i.e., the joint angular velocity reference, $\omega_{emg}$). As shown in FIG. 1, $\omega_{emg}$ is generated by a velocity reference generation module 108 based on the pre-processed the EMG signals, the current angle for the joint ($\theta_k$), the derivative or rate of change of angle for the joint ($\dot{\theta}_k$), and the user's intent to flex or extend the knee. The intent can be obtained from a flexing extending classification module 110. Thereafter, an equilibrium point joint angle $\dot{\theta}_{emg}$ can be obtained from $\omega_{emg}$ using conversion module 112. The equilibrium point joint angle, $\theta_k$, and $\dot{\theta}_k$ can then be used in a volitional impedance controller module 114 to generate a joint torque command ($\tau$) for the prosthesis 102 to cause motion of the knee joint. Additionally, $\theta_k$ and $\dot{\theta}_k$ are updated based on the torque command. The control process then repeats. It should be noted though that since $\theta_k$ and $\dot{\theta}_k$ are the measurements of the knee angle and velocity of the prosthesis, the update is not done computationally, rather it is a physical process. The operation of these various modules is described below in greater detail.

B. Volitional Impedance Controller

In the various embodiments, EMG is used to generate an angular velocity command (as is commonly the case in upper extremity myoelectric control) rather than a position command, so that the user contracts the residual limb musculature only to move the joint and can relax when maintaining any given knee joint angle. Specifically, the joint torque command at controller module 114 can be given by a model mimicking the behavior of a spring and dashpot element. For example, one model in accordance with the various elements can be:

$$\tau = k(\theta - \theta_{emg}) + b\dot{\theta} \quad (1)$$

where the equilibrium point $\theta_{emg}$ is given by module 112 using $$\theta_{emg} = \theta_0 + \int_t \omega_{emg} dt \quad (2)$$

where k is the prescribed joint stiffness, b is the prescribed joint damping coefficient, $\theta$ is the knee joint angle, and $\theta_o$ is the initial angle when the control system switches to the volitional (non-weight bearing) controller and $\omega_{emg}$ is the angular velocity reference generated from the quadriceps and hamstring EMG, as described in the following section.

C. Reference Velocity Generation

The controller module 114 utilizes the measured surface EMG from the quadriceps and hamstring groups to generate a joint angular velocity reference, $\omega_{emg}$, to drive the joint angular impedance equilibrium point, $\theta_{emg}$, and thus to drive the motion of the knee. One method for doing so at module 108 would be to use $$\omega_{emg} = \begin{cases} k_h e_h & \text{if } e_h \geq e_q \\ -k_q e_q & \text{otherwise} \end{cases} \quad (3)$$

where $e_h$ and $e_q$ represent the measured (i.e., rectified and filtered) EMG from the hamstring and quadriceps muscles, respectively, and $k_h$ and $k_q$ are simple gains. Equation (3) also assumes that an appropriate dead-band is applied to the measured EMG, to avoid "jitter" in the angular velocity reference command. Equation (3) is similar to the method used for the control of myoelectric upper extremity prostheses.

However, as shown below, use of equation (3) provided only marginal performance in the proposed volitional controller. Specifically, as described subsequently (and indicated in FIGS. 3A-3C), two of the three amputee subjects on which the approach was implemented demonstrated a significant degree of co-contraction when attempting to contract either the hamstrings or quadriceps in an isolated manner. With sufficient training, these subjects could possibly be trained to avoid co-contraction. Co-contraction, however, is a natural neuromuscular response (particularly in the lower limb musculature). As such, in an effort to render the proposed controller as natural as possible, in the various embodiments, the controller is trained to properly interpret co-contraction, rather than train the subjects to avoid it. Therefore, as indicated in the control structure of FIG. 1 and described below, the controller 100 first utilizes pattern classification to classify the user's intent with regard to flexion or extension of the knee, then utilizes a projection operator to extract the desired magnitude of the joint angular velocity reference from the measured EMG data.

D. Flexion-Extension Classification

As described above, rather than train the subjects to avoid co-contraction while commanding flexion or extension of the knee, the various embodiments utilize a pattern classification approach to distinguish user intent to flex or extend the knee. In one embodiment, module 110 can be implemented using a quadratic discriminant analysis (QDA) classifier to distinguish between the user's intent to flex or extend. A linear discriminant analysis (LDA) classifier can also applied to the classification problem in other embodiments, although the QDA was chosen due to improved classification accuracy (based on the mean accuracy obtained with a five-fold cross-validation for each subject), and because the QDA is not significantly more complex (or computationally expensive) than the LDA classifier. Specifically, QDA uses the quadratic decision boundary of the form $c_1 + c_2 e_h + c_3 e_q + c_4 e^2_h + c_5 e_h e_q + c_6 e^2_q = 0$ to classify the sample consisting of the processed EMG data from the two channels, $e_h$ and $e_q$, to the extension ($\omega_E$) and flexion ($\omega_F$) classes where the coefficients $c_i$, i=1, 2, . . . , 6, are generated during the training of the QDA classifier. Details of the LDA and QDA methods can be found in several pattern classification references. Further, this embodiment utilizes a database of EMG (versus intent) data to parameterize the flexion/extension classifier, as described below.

E. EMG Measurement and Preprocessing

In the various embodiments, the electrodes can be implemented in various ways. For example, as described above, surface EMG electrodes can be embedded into the prosthesis socket. In another implementation, separate surface electrodes can be placed on the amputee to acquire EMG signals from the residual quadriceps and hamstring muscles of the amputee subjects. To improve acquisition of such signals, the signals from each muscle group can amplified, filtered, and/or rectified at module 106. In other words, the EMG preprocessing attempts to discern an envelope of the raw EMG signal.

In the various embodiments, each EMG signal is acquired from a single bipolar electrode. Such signals are generally very small in magnitude and can have both positive and negative values when the muscle contracts. An instrumentation amplifier can then be used to increase the voltage levels of these signals. Thereafter, high pass filtering can be applied to remove the baseline noise and rectification can be done to remove the negative values. Finally, the signal can be low pass filtered to create an envelope of the signal. This way, the muscle contraction EMG signals will be converted to a unidirectional multilevel signal in expense of some phase delay due to the filtering. In other words, the preprocessing is done to convert the noisy raw EMG data to a less noisy form that is more suitable for controls and pattern recognition.

For example, in one embodiment, the signal can be processed using an instrumentation amplifier with a gain of 200 and filtered using an analog second order low pass filter with 5 Hz cutoff frequency. The filtered signals can then be digitized for use. For example, using a computer running MATLAB Real Time Workshop with a digital-to-analog converter card and operating at 1000 Hz sampling frequency. The digital signals can then be further processed using additional signal processing. For example, signals can be processed using a first order high-pass filter with 20 Hz cutoff frequency, a rectifier, and a first order low-pass filter with 2 Hz cutoff frequency.

F. EMG Intent Database Generation

Classifier training database generation can be performed by recording EMG data associated with an amputee. For example, in one embodiment, a training database can be generated for an amputee by recording 100 seconds of EMG data for knee flexion and 100 seconds for knee extension. For ease of the subject, a one-minute rest in between the recordings can be provided. Thus the entire training session can be configured to last less than five minutes. To generate a complete set of training data for each flexion/extension class, each subject can be asked to visualize extending the knee on the amputated side at 0, 25, 50, 75 and 100 percent of full effort, several times for durations ranging from 1 to 5 seconds, over the total data collection period of 100 seconds at a 100 Hz sampling frequency. The extension data can be recorded first, followed by a rest period of approximately one minute, followed by the same procedure for flexion data. All EMG data can be normalized into the interval [0, 1]. The data can be additionally thresholded at 20% maximum effort, such that samples in the interval [0, 0.2] are effectively removed from the database and in order to mitigate baseline EMG noise and muscular tonicity. Based on this thresholded database, the QDA classifier can be parameterized to classify each subject's preprocessed EMG as intent to either flex or extend the knee joint.

G. Reference Velocity Magnitude

The QDA essentially provides a probabilistic optimal separation boundary of the EMG data to the flexion and extension classes. Within a given class (in this case flexion or extension), the "magnitude" of the data is the projection along the principal axis of that class. In the control approach described herein, this projection can be generated via principal component analysis (PCA), which essentially projects the two-dimensional EMG data along a principal (either flexion or extension) axis. Using the data belonging to each class, two 2×2 PCA projection matrices $W_E$ and $W_F$ can be computed. In the real-time implementation, one of these projection matrices can be used to extract the "magnitude" information, based on the result of QDA classification as follows:

$$[x_p \ x_s]^T = \begin{cases} W_E [x_h \ x_q]^T & \text{if } \omega_E \\ W_F [x_h \ x_q]^T & \text{if } \omega_F \end{cases} \quad (4)$$

The magnitude of the angular velocity reference for the joint impedance set-point, $\omega_{emg}$, can therefore be the PCA-based projection of the two-dimensional EMG data along the principal axis of either the flexion or extension data. Details of PCA can be found in several references. The projected EMG data can be scaled between zero and maximum reference velocity to generate the desired angular velocity reference. The maximum reference velocity can be determined as the maximum reasonable angular velocity command for volitional control of the knee joint.

In contrast with (3), which obtains a reference angular velocity (for the volitional control impedance set-point) by projecting data along a hamstring/quadriceps set of measurement axes, the approach combining QDA classification with PCA projection of the two-dimensional EMG data establishes a probabilistically optimal linear transformation from a hamstring/quadriceps set of axes to a flexion/extension set of axes (based on the training dataset). As such, the subject need not be trained to isolate the contraction of individual muscle groups, but rather is free to co-contract the hamstring and quadriceps groups in a natural manner when intending knee flexion or extension.

II. Volitional Control of Powered Knee and Powered Ankle

A. Volitional Control Structure

Although the volitional control structure above describes how to provide volitional control of a powered knee joint, volitional control of a powered knee and a powered joint is desirable in many circumstances. In particular, volitional control of both the knee and ankle allows more natural motion and provides the user the option to manipulate the foot. Accordingly, in some embodiments, a control framework can be provided that is intended to provide volitional control of both the knee and ankle joints with a joint output impedance similar to that of the native limb. As such, rather than using the measured EMG solely to prescribe joint torque, angle, or angular velocity, the presented framework can utilize measured EMG to prescribe the angular velocity of an equilibrium point of joint impedance that consists of the combination of a joint stiffness and damping. In this manner, the knee can move to a desired position with a joint output stiffness and damping prescribed by the controller, thus presumably moving in a more natural manner (relative to a high-output-impedance position controller), and resulting in a more natural interaction between the user, prosthesis, and environment.

Figure 2:
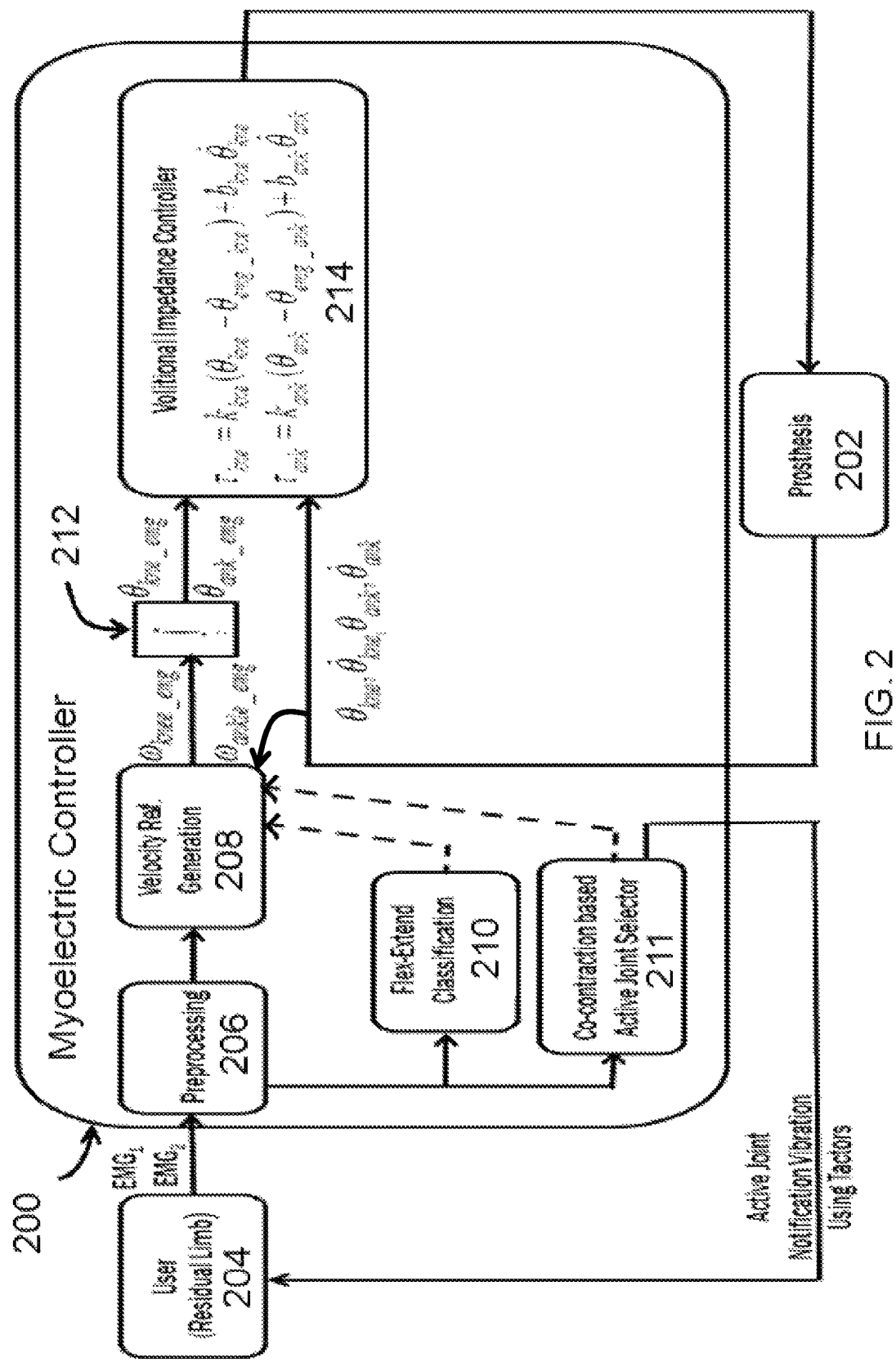
FIG. 2 shows a block diagram of a myoelectric volitional impedance controller for controlling a powered knee joint and a powered ankle joint in accordance with an embodiment.

The structure of the volitional controller for knee and ankle joints is shown in FIG. 2. FIG. 2 shows a block diagram of a myoelectric volitional controller 200 for controlling a prosthesis 202 having powered knee joint or a powered ankle joint in accordance with an embodiment. In many respects, the controller 200 operates in a substantially similar fashion to controller 100 in FIG. 1. That is, during a non-weight bearing activity, based on an intent recognizer (not shown), EMG signals ($EMG_1$, $EMG_2$) are received by controller 200 from the residual limb of the user 204. Thereafter, a pre-processing module 206 processes the EMG signals. The pre-processed signals are then used for generation of reference velocities for the knee or the ankle joints (i.e., one of joint angular velocity references, $\omega_{knee\_emg}$ and $\omega_{ankle\_emg}$, respectively). As shown in FIG. 2, the one of $\omega_{knee\_emg}$ and $\omega_{ankle\_emg}$ is generated by a velocity reference generation module 208 based on the pre-processed EMG signals, the user's intent to flex or extend the knee, a user selection of a joint, and a corresponding current angle for the joint to be controlled ($\theta_{kne}$ or $\theta_{ank}$), the derivative or rate of change of angle for the joint to be controlled ($\dot{\theta}_{kne}$ or $\dot{\theta}_{ank}$). The intent can be obtained from a flexing extending classification module 210. The user selection can be based on detection of co-contraction or a "twitch" using module 211. Thereafter, an equilibrium point joint angle for the one of the knee ($\theta kne\_emg$) or the ankle ($\theta_{ank\_emg}$) can be obtained from a corresponding one of $\omega_{knee\_emg}$ and $\omega_{ankle\_emg}$ using conversion module 212. The one equilibrium point joint angle can then be used in a volitional impedance controller module 214 to generate a joint torque command ($\tau$) for the prosthesis 102 to cause motion of the knee or ankle joint. Additionally, the resulting values for $\theta_{kne}$, $\theta_{ank}$, $\dot{\theta}_{kne}$ and $\dot{\theta}_{ank}$ are updated. The control process then repeats. The operation of these various modules is described below in greater above and below, as necessary.

B. Volitional Impedance Controller

Controller module 214 here operates in a manner substantially similar to that of controller module 114 in FIG. 1. Again, it is noted that the EMG is used to generate an angular velocity command (as is commonly the case in upper extremity myoelectric control) rather than a position command, so that the user contracts the residual limb musculature only to move the joint and can relax when maintaining any given knee joint angle. Specifically, the joint torque command at controller module 214 is given by:

$$\tau_{kne} = k_{kne}(\theta_{kne} - \theta_{emg\_kne}) + b_{kne}\dot{\theta}_{kne}$$

$$\tau_{ank} = k_{ank}(\theta_{ank} - \theta_{emg\_ank}) + b_{ank}\dot{\theta}_{ank} \quad (5)$$

where the knee and ankle equilibrium points $\theta_{kne\_emg}$ and $\theta_{ank\_emg}$ are given by $$\theta_{kne\_emg} = \theta_{o\_kne} + \int_t \omega_{kne\_emg} dt \quad (6)$$

$$\theta_{ank\_emg} = \theta_{o\_ank} + \int_t \omega_{ank\_emg} dt$$

where $k_{kne}$ and $k_{ank}$ are the prescribed joint stiffnesses, $b_{kne}$ and $b_{ank}$ are the prescribed joint damping coefficient, $\theta_{kne}$ and $\theta_{ank}$ are the knee and ankle joint angles, and $\theta_{o\_kne}$ and $\theta_{o\_ank}$ are the initial knee and ankle angles when the control system switches to the volitional (non-weight bearing) controller. $\omega_{kne\_emg}$ and $\omega_{ank\_emg}$ are the knee and ankle angular velocity references generated from the quadriceps and hamstring EMG, as described in the following section.

C. Active Joint Selection Using Twitch

Figure 5:
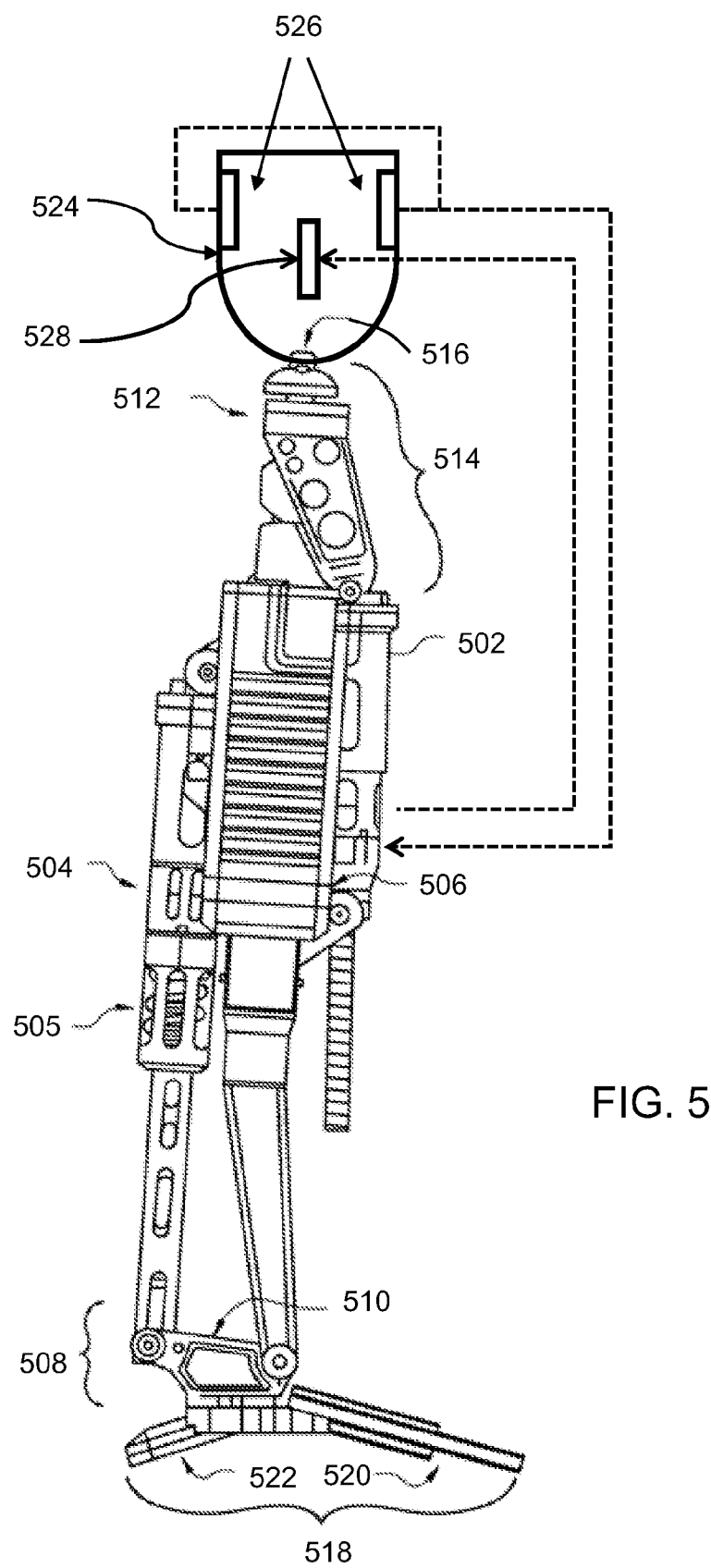
FIG. 5 is a schematic illustration of an exemplary powered transfemoral prosthesis that can be configured for using a control system in accordance with the various embodiments.
Figure 6B:
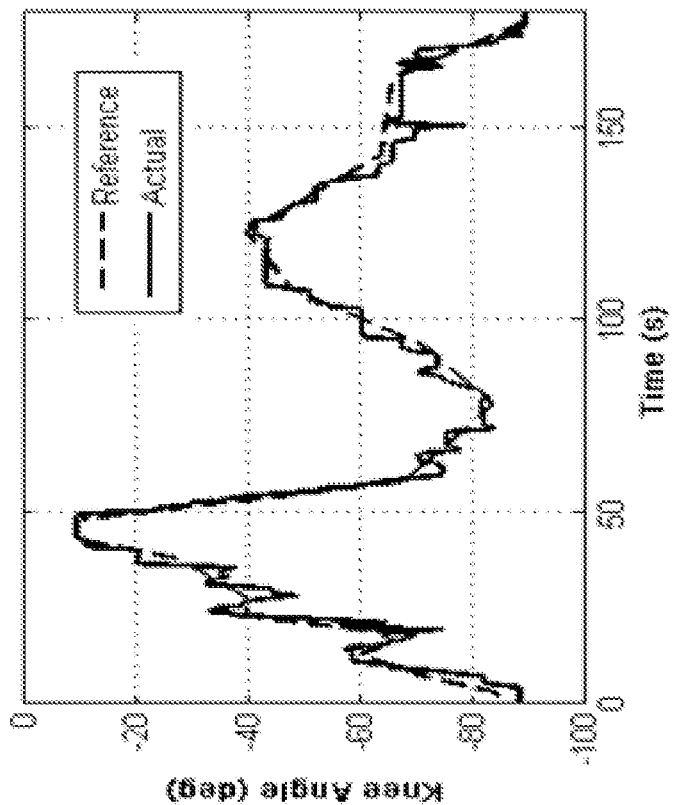
FIGS. 6A-6D show x-y plots of EMG-controlled powered prosthesis knee position for trajectories A-D, respectively, of the third amputee subject in FIG. 3C.
Figure 6A:
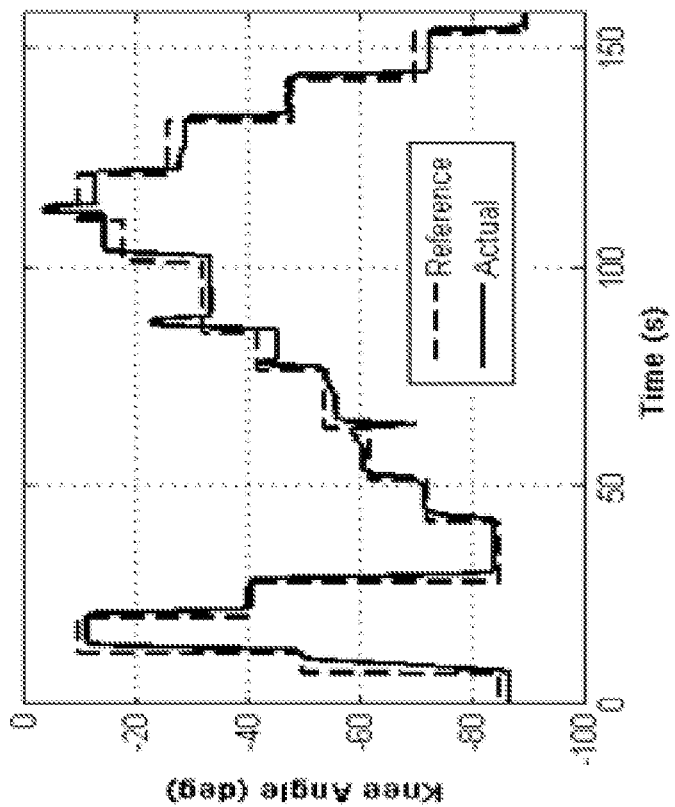
Figure 6D:
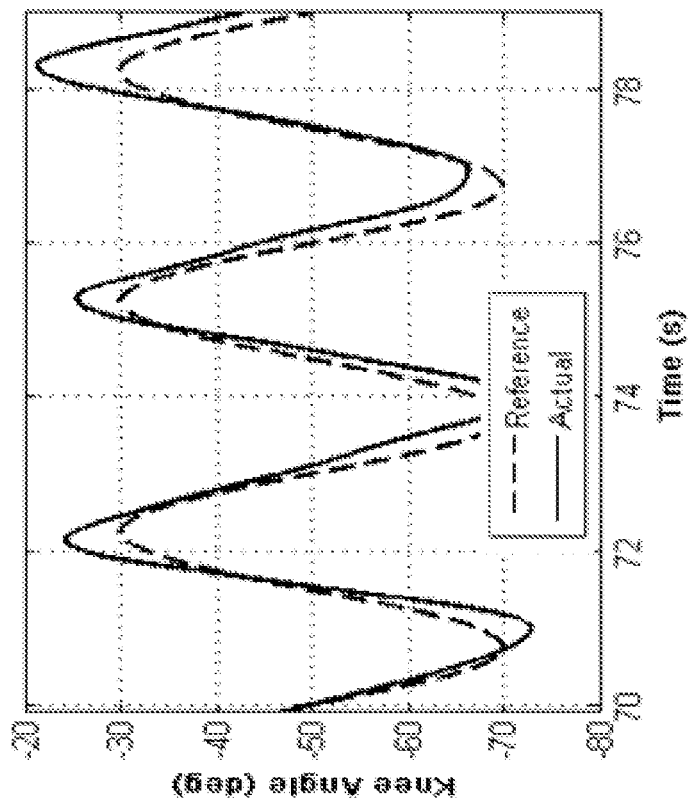
Figure 6C:
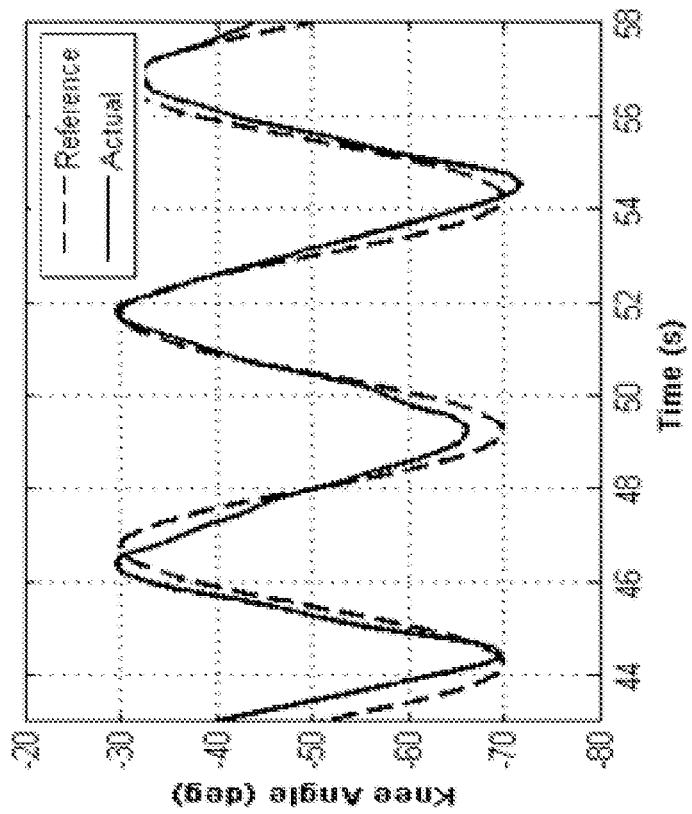
Figure 7B:
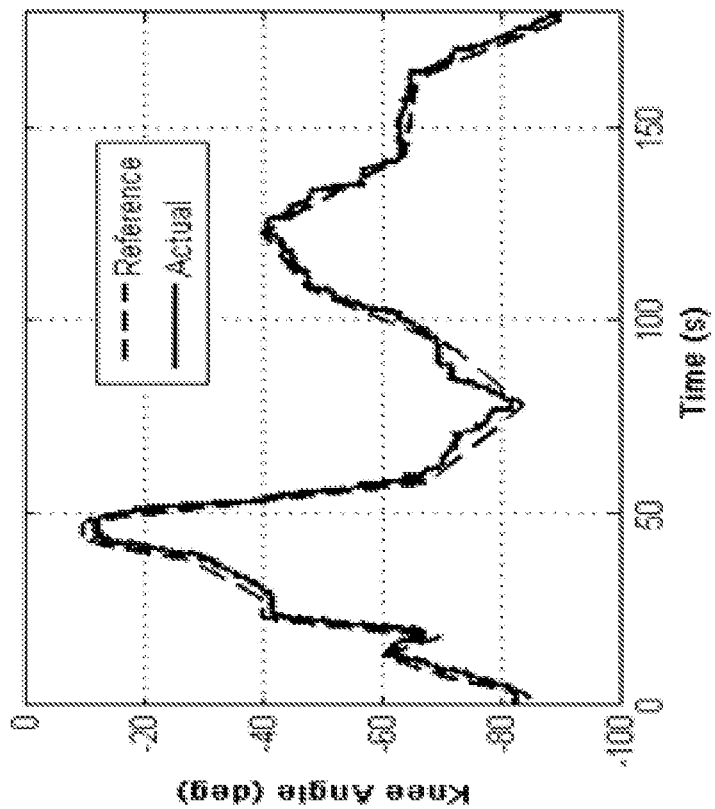
FIG. 7A-7D show x-y plots of sound-side knee position for trajectories A-D, respectively, of the third amputee subject in FIG. 3C.
Figure 7A:
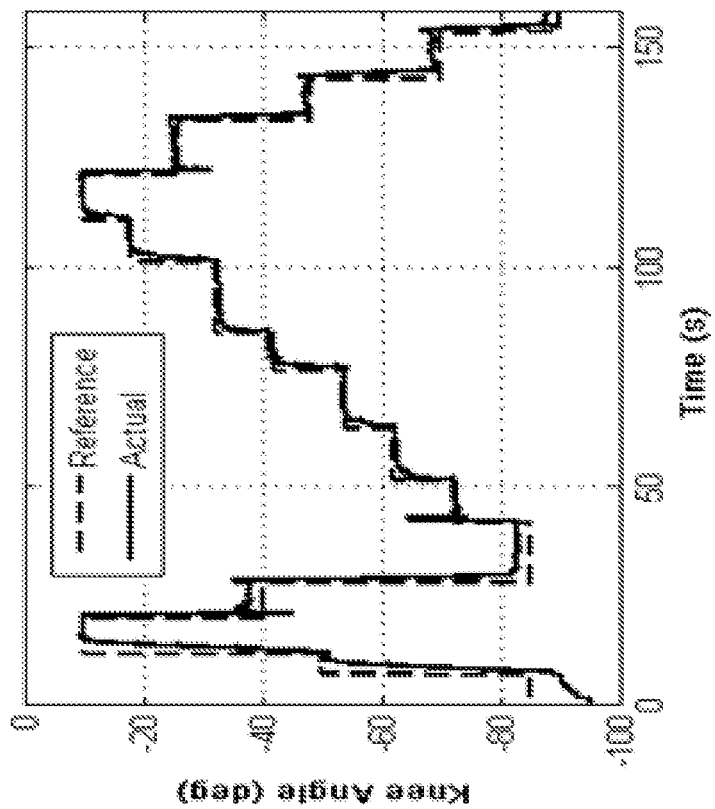
Figure 7C:
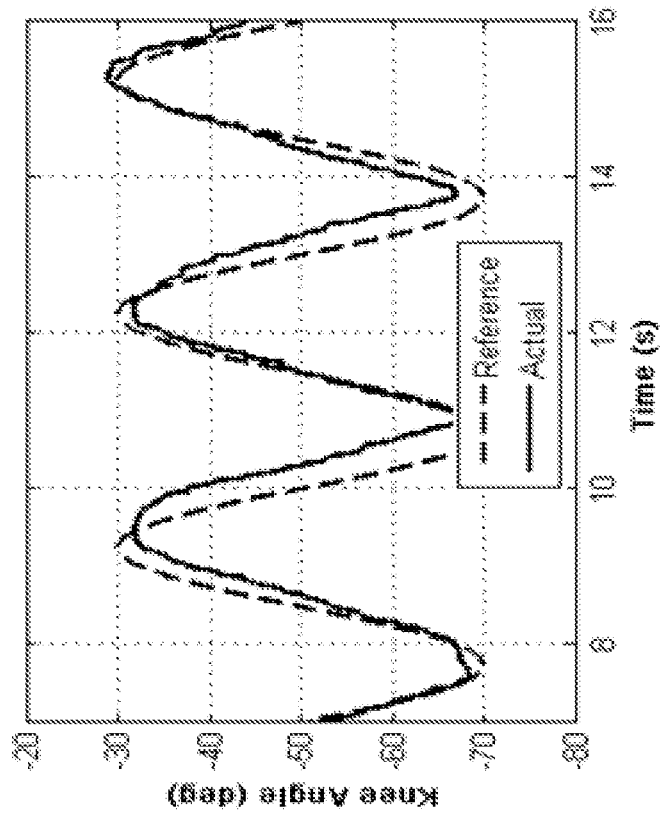
Figure 7D:
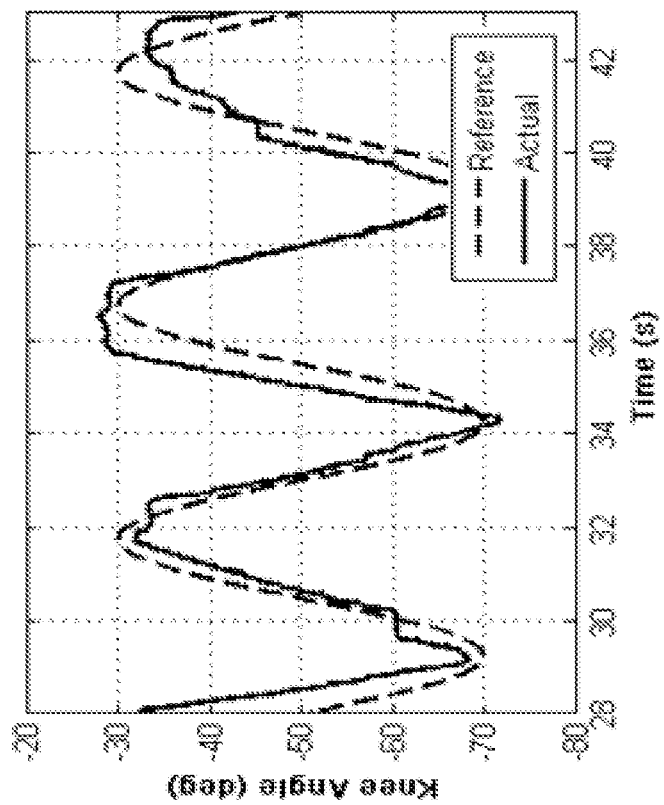

In this embodiment, two unidirectional EMG channels are used to generate two bidirectional joint velocity references, one for the ankle joint and one for the knee joint of the prosthesis. In one embodiment, one bidirectional signal for one of the joints is generated at a single instant. In order to achieve this, a short duration co-contraction (twitch) of the both EMG electrode sites can be utilized to select the active joint. A twitch can be detected when the filtered and rectified EMG signals on both channels exceed a threshold for a short duration of time. Once a twitch is detected the active joint of the prosthesis can be toggled. One of the two tactors (e.g. cellphone vibration motor) on the residual limb (or in the socket as shown in FIG. 5 below) can then be activated for a short duration to notify the user which joint is active.

D. Flexion-Extension Classification

Once the active joint is selected, the user intent to flex or extend can be detected using a pattern classification algorithm in module 210, as described above with respect to module 110 in FIG. 1. For example, such algorithms can include linear discriminant analysis (LDA), quadratic discriminant analysis (QDA), support vector machines (SVM) or artificial neural networks (ANN). In order to generate the flexion extension classification boundaries (or functions) a database of different intensity flexion and extension EMG data from hamstring and quadriceps muscles need to be collected, as described above. This data can then be used to train the pattern classifiers.

D. Reference Velocity Magnitude

Once the user intent to flex and extend is inferred, the joint velocity reference magnitude can be obtained at module 208 as a function of the filtered EMG signals. One possible way to generate the velocity references might be to use principal component analysis to project the two dimensional filtered EMG signals to the one dimensional principal component.

III. Experimental Implementation

A. EMG-Based Reference Velocity Generation

The proposed volitional knee joint controller of FIG. 1 was implemented on three transfemoral amputee subjects. The subjects were all male, between the ages of 20 and 60, and between 3 months and 4 years post amputation. Two of the subjects were unilateral transfemoral amputees, while one subject (subject 3) was a bilateral amputee, with a transfemoral amputation on one leg and a transtibial on the other. In all cases, all subjects were characterized by a prosthetic knee on one limb and an intact knee on the other.

Figure 3A:
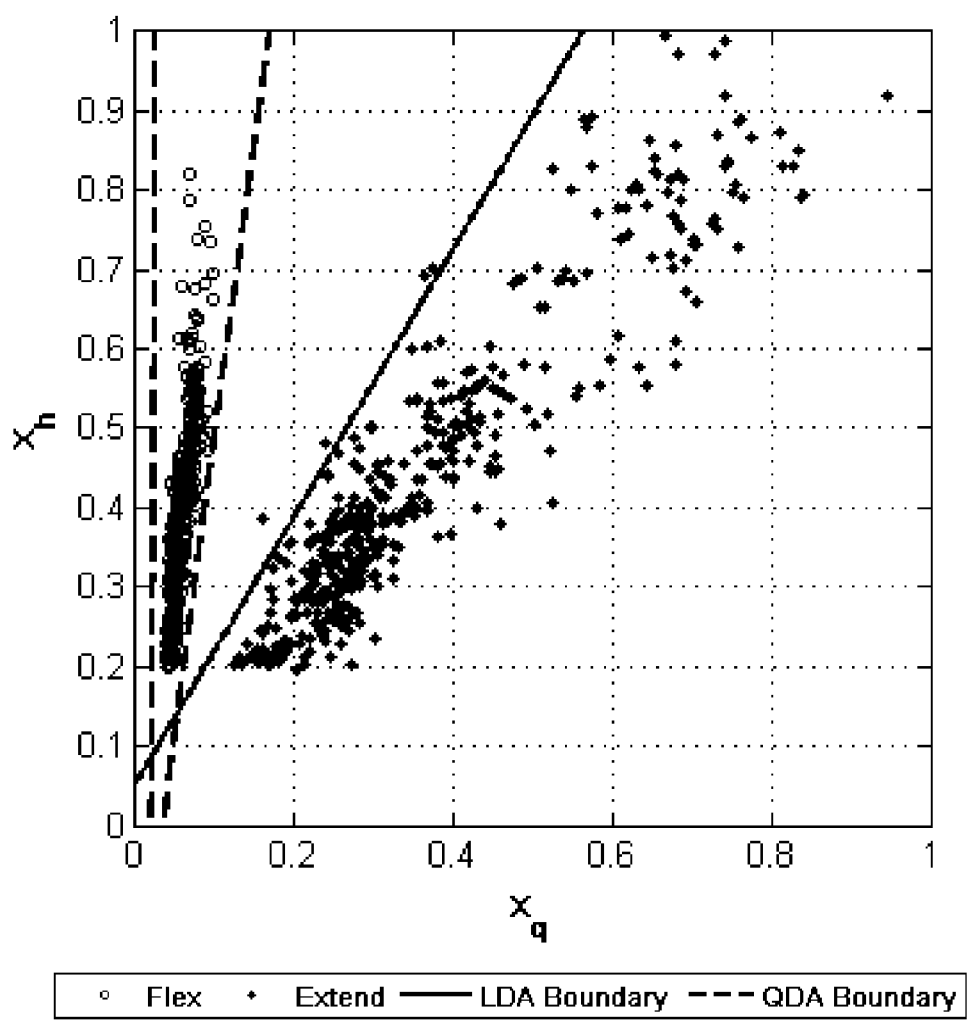
FIG. 3A is an x-y plot of extension and flexion reference signals for a first amputee subject showing classification using quadratic discriminant analysis (QDA) and linear discriminant analysis (LDA) methods in accordance with the various embodiments.
Figure 3B:
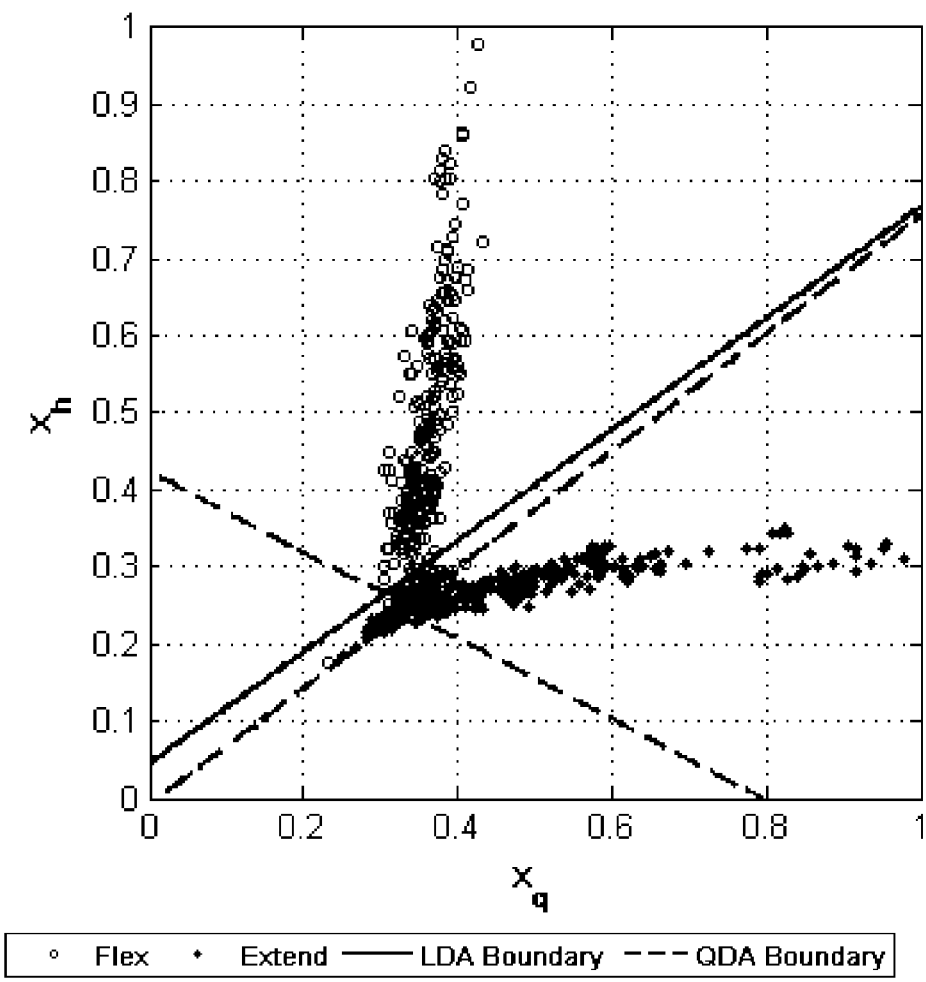
FIG. 3B is an x-y plot of extension and flexion reference signals for a second amputee subject showing classification using QDA and LDA methods in accordance with the various embodiments.
Figure 3C:
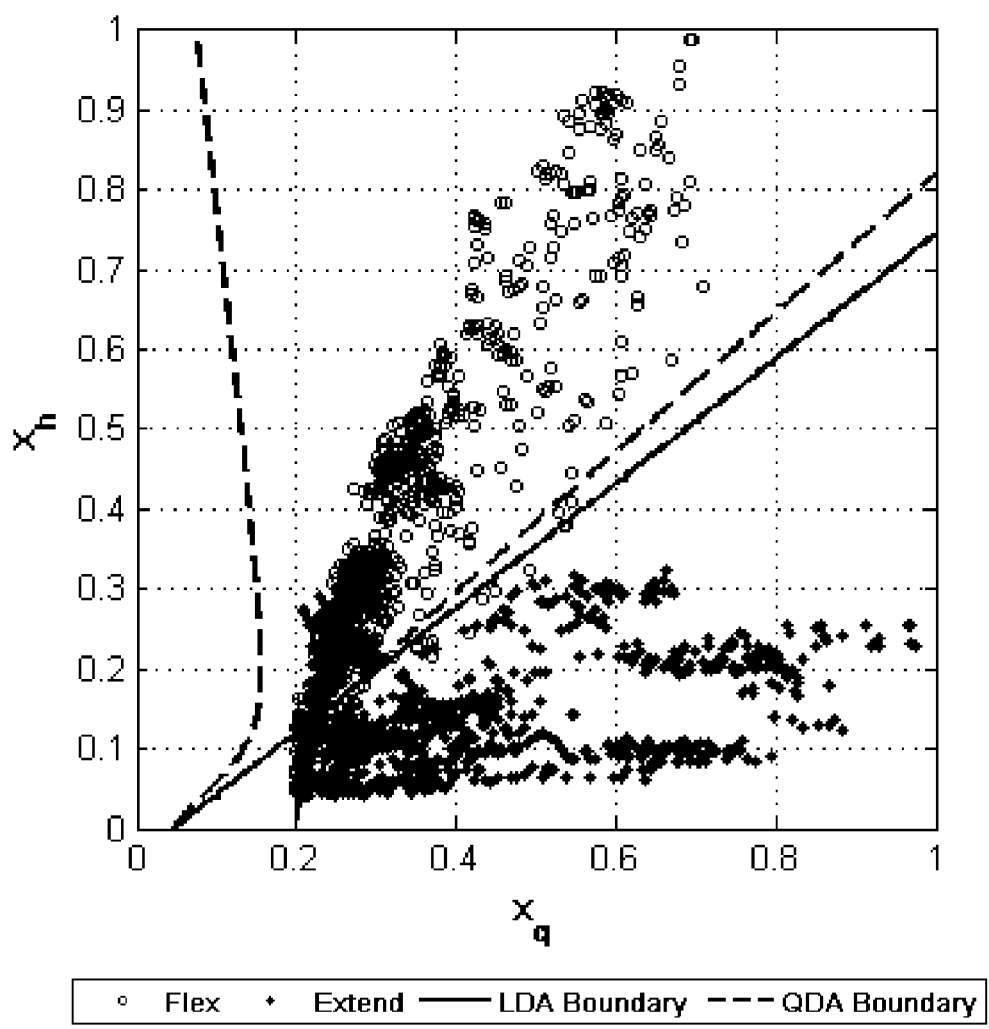
FIG. 3C is an x-y plot of extension and flexion reference signals for a third amputee subject showing classification using QDA and LDA methods in accordance with the various embodiments.

FIGS. 3A-3C shows the EMG intent databases corresponding to each subject. In particular, FIG. 3A is an x-y plot of extension and flexion reference signals for a first amputee subject (subject 1) showing classification using QDA and LDA methods in accordance with the various embodiments. FIG. 3B is an x-y plot of extension and flexion reference signals for a second amputee subject (subject 2) showing classification using QDA and LDA methods in accordance with the various embodiments. FIG. 3C is an x-y plot of extension and flexion reference signals for a third amputee subject (subject 3) showing classification using QDA and LDA methods in accordance with the various embodiments.

These databases, as described above, correspond to 100 seconds of flexion data at various degrees of (muscular) effort, and 100 seconds of extension data, also at various degrees of effort. Note that the $x_q$ axis represents the measured, preprocessed, normalized, and thresholded EMG for the quadriceps group, while the $x_h$ axis represents the EMG measured for the hamstring group. As seen in FIGS. 3A-3C, two of the three subjects (subjects 1 and 3) demonstrated a significant amount of muscular co-contraction when intending volitional movement of the prosthetic knee. Interestingly, subject 1 primarily demonstrated significant co-contraction during intent to extend the knee, while subject 3 primarily demonstrated significant co-contraction during intent to flex the knee. For all subjects, the LDA and QDA boundaries between classes along with the pseudo-classification boundary described by (3) are shown in the figures. Recall that, based on a five-fold cross-validation of classification accuracy, QDA classification in general provided higher classification accuracies, and therefore was used in the control experiments to classify intent to flex or extend the knee. Specifically, the mean accuracies of the classifiers over 5 CV-fold for each of the three subjects are 0.99, 0.80 and 0.86 for the LDA and 1.0, 0.86 and 0.90 for the QDA. Note that, particularly in the cases of subjects 1 and 3, the simple thresholding approach (described by (3)) entails a considerable amount of erroneous "classification" of intent, even in the case of large amplitude EMG ($x_i > 0.3$). In contrast, the QDA classification boundaries entail little to no classification error, particularly in large amplitude EMG.

Figure 4B:
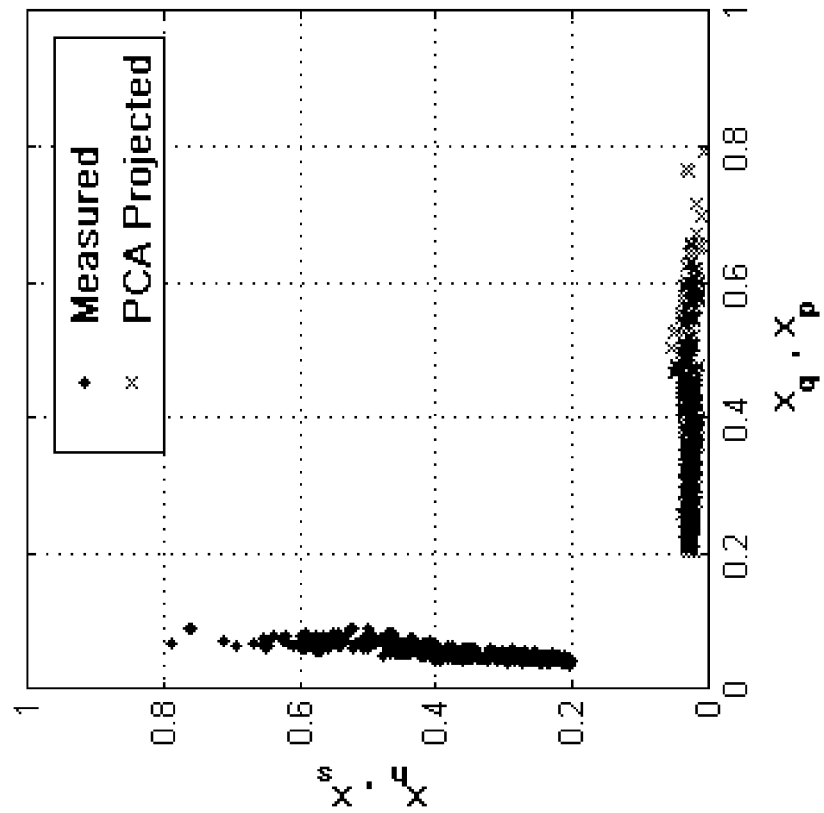
FIG. 4B is an x-y plot of actual measurements and PCA projections of flexion reference signals for the first amputee subject in FIG. 3A.
Figure 4A:
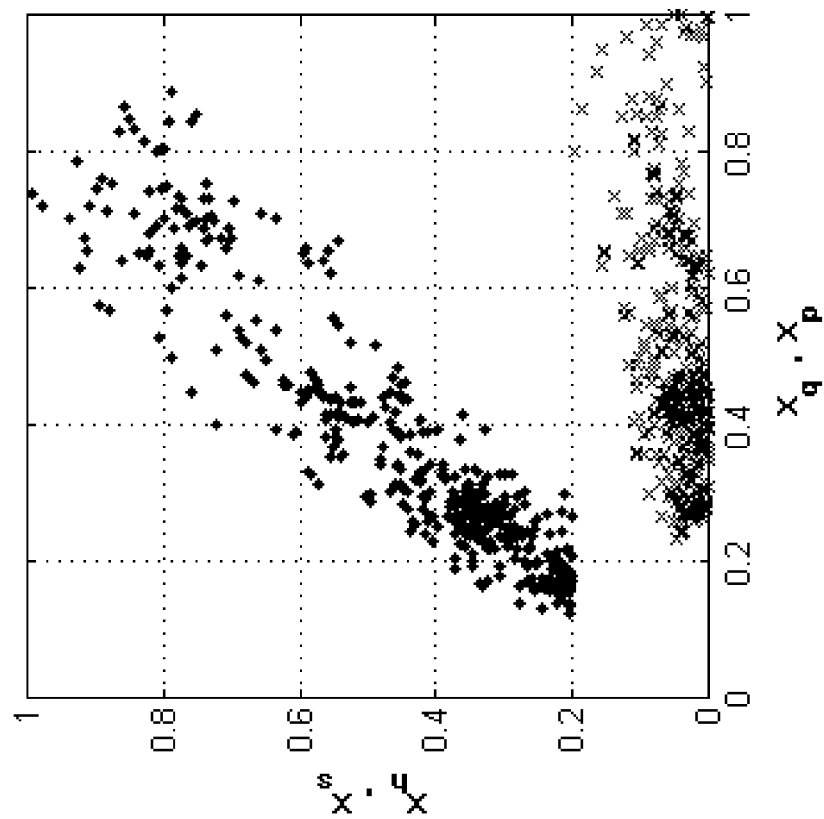
FIG. 4A is an x-y plot of actual measurements and PCA projections of extension reference signals for the first amputee subject in FIG. 3A.

Once intent to flex or extend the knee is known, the magnitude of the angular velocity for the impedance set-point is obtained by projecting the corresponding data point onto its principal axis via PCA. A representative example of the corresponding PCA projections for subject 1 is shown in FIGS. 4A and 4B. FIG. 4A is an x-y plot of actual measurements and PCA projections of extension reference signals for the first amputee subject in FIG. 3A. FIG. 4B is an x-y plot of actual measurements and PCA projections of flexion reference signals for the first amputee subject in FIG. 3A. In the figures, the $x_p$ axis corresponds to the PCA projection of the flexion and extension data along the principal component of that data. As such, the angular velocity for the impedance set-point of the volitional knee joint controller can be given by:

$$\omega_{emg} = \begin{cases} 0 & \text{if } \omega_F \text{ and } (x_P < \gamma) \\ \alpha\left(\frac{x_P - \gamma}{1 - \gamma}\right) & \text{if } \omega_F \text{ and } (x_P \geq \gamma) \\ 0 & \text{if } \omega_E \text{ and } (x_P < \gamma) \\ -\alpha\left(\frac{x_P - \gamma}{1 - \gamma}\right) & \text{if } \omega_E \text{ and } (x_P \geq \gamma) \end{cases} \quad (7)$$

where α is the maximum desired set-point velocity (corresponding to maximum muscular effort), γ is the value at which the normalized EMG is thresholded (in this case γ=0.2), $x_p$ is the PCA projection along the principal axis. For the actual samples, $x_q$ and $x_h$ denote the normalized EMG signals for the quadriceps and hamstrings muscles, respectively. For the PCA projections, $x_p$ and $x_s$ denote the first principal and second principal components, respectively.

B. Volitional Trajectory Tracking of a Powered Knee Prosthesis

The volitional knee controller of FIG. 1 was implemented on each of the three amputee subjects with the powered transfemoral prosthesis 500 shown in FIG. 5 and described in detail in U.S. patent application Ser. No. 12/427,384 to Goldfarb et al, filed Apr. 21, 2009, the contents of which are herein incorporated in their entirety. However, the various embodiments are not limited to any particular design of a prosthesis. Thus, other designs can be used with the various embodiments.

As shown in FIG. 5, prosthesis 500 includes a knee actuation unit 502 for actuating a knee joint 514, an ankle actuation unit 504 for actuating an ankle joint 508, and an embedded system 506 housing, for example, a battery and the controller module or system. Both the knee joint 514 and ankle joint 508 can incorporate integrated potentiometers for joint angle position. The ankle actuation unit can include a spring 505. One 3-axis accelerometer is located on the embedded system 506 and a second is located below the ankle joint 508 on the ankle pivot member 510. A strain based sagittal plane moment sensor 512 can located between the knee joint 514 and the socket connector 516, which measures the moment between a socket 524 and the prosthesis 500. Prosthesis also includes a foot 518 designed to measure the ground reaction force components at the ball 520 of the foot and heel 522. Each of heel 522 and ball 520 incorporates a full bridge of semiconductor strain gages that measure the strains resulting from the respective ground contact forces. The prosthetic foot can be designed to be housed in a soft prosthetic foot shell (not shown).

As noted above, The prosthesis used in these experiments also contains a powered ankle, although the ankle was not explicitly commanded in these experiments, but rather remained in a "neutral" configuration. In order to characterize the effectiveness of the volitional controller for purposes of moving the knee joint, an experiment was developed which required each subject to track various types of knee joint angle movements. During these experiments, each amputee was presented with a computer monitor that showed in real-time a desired knee angle, along with the knee angle of the powered prosthesis, as measured by the joint angle sensor on the prosthesis.

Prosthesis sockets with embedded EMG electrodes for each subject were not available for these experiments. Normally, such EMG electrodes would be disposed similarly to the configuration illustrated in FIG. 5 in order to correspond with locations of the residual portions of the hamstring and/or quadriceps on an amputee. That is, referring back to FIG. 5, the socket 524 for prosthesis 500 would be configured to include electrodes 526 positioned along inner surfaces of socket 524 and at locations such that the user's hamstring and/or quadriceps would come into contact with electrodes 526. Signals from electrodes 526 would then be provided to the embedded system 506. Additionally, to allow the embedded system 506 to provide feedback to the user as to which joint is active, a tactor 528, coupled to embedded system 506, would be embedded into socket 524, as described above.

However, since the various embodiments of the volitional controller are intended for non-weight-bearing activity such as sitting, the subjects did not wear the powered prosthesis during the knee control experiments, but rather the subjects were seated in a chair and the powered knee prosthesis was mounted to a bench immediately next to the subject. The prosthesis was mounted in an orientation that was consistent with the seated position of the subjects.

Aside from the QDA and PCA parameters extracted from the EMG intent database, all subjects utilized the same set of volitional control parameters for the powered prosthesis. Specifically, the stiffness of the impedance controller was selected as k=1.0 Nm/deg, the damping as b=0.01 Nm/deg/s, the maximum set-point velocity α=50 deg/s. These parameters were selected experimentally to provide an acceptable bandwidth of motion, while maintaining a natural appearance of motion and a stable interaction with obstacles in the environment (e.g., the leg of a chair).

In order to characterize volitional control of various types of motion, four different desired trajectories were constructed (referred herein as trajectories A through D). The trajectory A joint angle tracking task consisted of set point trajectories requiring the subject to quickly change the knee angle in 8 to 45 degree increments and to hold it for 5 to 10 seconds. Trajectory B consisted of sloped trajectories, which were intended to measure the subject's ability to move the prosthesis at different constant velocities. Trajectories C and D consisted of sinusoidal waves at 0.2 and 0.33 Hz, respectively (i.e., five-second and three-second periods, respectively), which were intended to measure the subject's ability to move the leg up and down smoothly at continuously varying velocities. Trajectories A and B lasted for a total duration of 160 and 180 seconds, respectively, while trajectories C and D lasted for a total duration of 60 seconds each.

For each amputee subject, three sessions of experiments were conducted, each on a different day, with each successive session approximately one week apart. During the experimental sessions, the amputee spent approximately one hour practicing the tracking of the four trajectories (A through D), during which the various trajectories were presented to the amputee in an arbitrary order. After completion of the third session (i.e., after approximately one hour of practice in the third session), the subject's performance was evaluated in a single set of performance tests, consisting of one trial each of trajectories A through D. Representative trajectory tracking performance data corresponding to subject 3, whose average performance was between that of subjects 1 and 2, is shown in FIGS. 6A-6D. FIG. 6 show x-y plots of EMG-controlled powered prosthesis knee position for trajectories A-D, respectively, of the third amputee subject in FIG. 3C.

The root-mean-square (RMS) trajectory tracking error for all amputee subjects for each of the four trajectories is summarized in Table I. As seen in the table, the average RMS tracking error across all subjects and all trajectories was 6.2 deg.

TABLE I

RMS ERROR FOR EMG CONTROL OF POWERED KNEE

| | Subject 1 EMG | Subject 2 EMG | Subject 3 EMG | EMG Control Avg. |
|---|---|---|---|---|
| Trajectory A | 6.8 | 8.2 | 8.0 | 7.7 |
| Trajectory B | 2.5 | 3.9 | 3.7 | 3.4 |
| Trajectory C | 4.4 | 7.2 | 5.3 | 5.6 |
| Trajectory D | 8.4 | 8.3 | 7.1 | 7.9 |
| Subject Avg. | 5.5 | 6.9 | 6.0 | 6.2 |

B. Comparison to Intact Knee Trajectory Tracking

In order to provide context for the trajectory tracking data summarized in Table I, corresponding experiments were conducted to assess the ability of each amputee to track the same set of knee joint angle trajectories with his sound knee. These experiments were conducted in a single session, since familiarization with the prosthesis and volitional impedance controller was not necessary (i.e., each subject was already quite familiar with the movement control of his sound knee). As such, each subject spent approximately 15 minutes practicing each set of trajectories, until each was comfortable with his ability to track the trajectories. Once sufficiently comfortable, each subject's performance was evaluated in a single set of performance tests, consisting of one trial each of trajectories A through D. Movement of the subjects' sound knee was measured by using a knee brace instrumented with a goniometer. The knee brace did not impose any significant constraints on knee movement. Representative data corresponding to subject 3 (whose prosthetic side data is shown in FIGS. 6A-6D) is shown in FIGS. 7A-7D. FIGS. 7A-7D shows x-y plots of sound-side knee position for trajectories A-D, respectively, of the third amputee subject in FIG. 3C.

The RMS trajectory tracking error for sound side knee angle tracking for all subjects for each of the four trajectories is summarized in Table II.

TABLE II

| RMS ERROR FOR VOLITIONAL CONTROL OF INTACT KNEE | | | |
|---|---|---|---|
| | Subject 1 Sound | Subject 2 Sound | Subject 3 Sound | Sound Side Avg. |
| Trajectory A | 6.1 | 6.8 | 7.6 | 6.8 |
| Trajectory B | 1.4 | 1.8 | 3.1 | 2.1 |
| Trajectory C | 4.6 | 6.1 | 6.4 | 5.7 |
| Trajectory D | 4.5 | 6.4 | 7.7 | 6.2 |
| Subject Avg. | 4.2 | 5.3 | 6.2 | 5.2 |

As seen in Table II, the average RMS tracking error across all subjects and all trajectories for sound knee tracking was 5.2 deg. Recall from Table I that the average RMS tracking error across all subjects and all trajectories for the EMG-based prosthesis knee tracking was 6.2 deg, thus indicating a difference in tracking error between the prosthetic and intact knee joints of one degree. As such, as indicated collectively by the tracking data, the ability of the amputee to control non-weight-bearing knee joint motion of the powered prosthesis (with the EMG-based impedance controller) is nearly as good as their ability to control non-weight-bearing knee joint motion in their intact knee. Further, the performance differences were fairly invariant with respect to movement type. Specifically, the average RMS errors for trajectory 4 (steps) were 7.7 deg and 6.8 deg, respectively, for the prosthetic and intact joints, and thus the difference in average error was 0.9 deg. The average RMS errors for trajectory B (ramps) were 3.4 deg and 2.1 deg, respectively, for the prosthetic and intact joints, and thus the difference in average error was 1.3 deg. For trajectory C (the slower sinusoid), the average RMS errors were 5.6 deg and 5.7 deg, respectively, for the prosthetic and intact joints, and thus the tracking performance for the slower sinusoid was essentially the same for the prosthetic and intact joint control. Finally, for trajectory D (the faster sinusoid), the average RMS errors were 7.9 deg and 6.2 deg, respectively, for the prosthetic and intact joints, and thus the prosthesis controller demonstrated 1.7 deg more error on average than the intact joint.

The resulting control approach shows that the resulting volitional control provides trajectory tracking performance close to that of their respective intact knee joints, thus indicating that the approach provides effective control of knee joint motion during non-weight-bearing activity.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A myoelectric controller for a weight bearing member having at least one powered joint, comprising:
   a non-transitory computer-readable medium;
   a velocity reference module stored in the computer-readable medium and configured for receiving myoelectric control signals from a user during a non-weight bearing mode for the at least one powered joint and generating a velocity reference for the at least one powered joint based on the myoelectric control signals;
   a volitional impedance module stored in the computer-readable medium and configured for generating a torque control signal for actuating the at least one powered joint based at least on the velocity reference; and
   a classification module stored in the computer-readable medium and configured for determining an intent of the user based on one of quadratic discriminant analysis of the myoelectric control signals and linear discriminant analysis of the myoelectric control signals,
   wherein the velocity reference module uses the intent of the user determined by the classification module to generate the velocity reference.

2. The myoelectric controller of claim 1, wherein the volitional impedance module generates the torque control signal using a model based on a behavior of a spring and dashpot element.

3. The myoelectric controller of claim 1, wherein the velocity reference module is further configured for generating the velocity reference based on a principal component analysis of the myoelectric control signals.

4. The myoelectric controller of claim 1, further comprising a pre-processing module stored in the computer-readable medium and configured for receiving raw myoelectric signals from the user and processing the raw myoelectric signals to yield the myoelectric control signals.

5. The myoelectric controller of claim 4, wherein the pre-processing module is configured for processing the raw myoelectric signals using at least one of amplification, filtering, or rectification.

6. The myoelectric controller of claim 1, wherein the volitional impedance module generates the torque control signal based on an equilibrium point derived from the velocity reference.

7. The myoelectric controller of claim 6, further comprising a conversion module stored in the computer-readable medium and configured for determining the equilibrium point based at least one of the velocity reference or an initial angle of the at least one powered joint.

8. A method for controlling for a weight bearing member having at least one powered joint, comprising:
receiving myoelectric control signals from a user during a non-weight bearing mode for the at least one powered joint and generating a velocity reference for the at least one powered joint based on the myoelectric control signals;
generating a torque control signal for actuating the at least one powered joint based at least on the velocity reference; and
determining an intent of the user based on one of quadratic discriminant analysis of the myoelectric control signals and linear discriminant analysis of the myoelectric control signals,
wherein the intent of the user is used to generate the velocity reference.

9. A non-transitory computer-readable medium having stored thereon a plurality of instructions for causing a computing device to control a weight bearing member having at least one powered joint, the plurality of instructions comprising code sections for causing the computing device to:
receive myoelectric control signals from a user during a non-weight bearing mode for the at least one powered joint and generating a velocity reference for the at least one powered joint based on the myoelectric control signals;
generate a torque control signal for actuating the at least one powered joint based at least on the velocity reference; and
determine an intent of the user based on one of quadratic discriminant analysis of the myoelectric control signals and linear discriminant analysis of the myoelectric control signals,
wherein the intent of the user is used to generate the velocity reference.

\* \* \* \* \*